United States Patent
Bhargava et al.

(10) Patent No.: US 11,834,405 B2
(45) Date of Patent: Dec. 5, 2023

(54) HEXANE AS A BY-PRODUCT OF ISOMERIZATION UNIT USING A DIVIDING WALL COLUMN

(71) Applicants: Sulzer Management AG, Winterthur (CH); BHARAT PETROLEUM CORPORATION LIMITED, Mumbai (IN)

(72) Inventors: Manish Bhargava, Katy, TX (US); Roomi Kalita, Houston, TX (US); Amit Kanda, Katy, TX (US); Pamaraju V Ravitej, Mumbai (IN); Kondapalli Shreya Chaudhary, Mumbai (IN)

(73) Assignees: BHARAT PETROLEUM CORPORATION LIMITED, Mumbai (IN); SULZER MANAGEMENT AG, Winterthur (CH)

( * ) Notice: Subject to any disclaimer, the term of this patent is extended or adjusted under 35 U.S.C. 154(b) by 46 days.

(21) Appl. No.: 17/609,521

(22) PCT Filed: May 14, 2020

(86) PCT No.: PCT/IB2020/000379
§ 371 (c)(1),
(2) Date: Nov. 8, 2021

(87) PCT Pub. No.: WO2020/229892
PCT Pub. Date: Nov. 19, 2020

(65) Prior Publication Data
US 2022/0227688 A1 Jul. 21, 2022

Related U.S. Application Data

(60) Provisional application No. 62/848,217, filed on May 15, 2019.

(51) Int. Cl.
*C07C 7/04* (2006.01)
*C07C 7/163* (2006.01)
(Continued)

(52) U.S. Cl.
CPC .............. *C07C 7/005* (2013.01); *B01D 3/141* (2013.01); *B01D 3/143* (2013.01);
(Continued)

(58) Field of Classification Search
None
See application file for complete search history.

(56) References Cited

U.S. PATENT DOCUMENTS

| 6,395,950 | B1 * | 5/2002 | Rice | C07C 9/16 585/737 |
| 6,395,951 | B1 * | 5/2002 | Hamm | B01D 3/141 585/827 |

(Continued)

FOREIGN PATENT DOCUMENTS

| CN | 103370397 A | 10/2013 |
| CN | 104093466 A | 10/2014 |

(Continued)

OTHER PUBLICATIONS

A. G. Faskhutdinov et al.; "Improvement of resource efficiency of the catalytic isomerization process by mathematical modeling"; Data Science; IV International Conference on "Information Technology and Nanotechnology" (ITNT-2018); c. 2018; pp. 377-383.

(Continued)

*Primary Examiner* — Tam M Nguyen
(74) *Attorney, Agent, or Firm* — GLOBAL IP COUNSELORS, LLP (57) ABSTRACT

A dividing wall column system for producing hexane includes a dividing wall column including a dividing wall that divides the dividing wall column at least partially into (Continued)

a first side and a second side, with one side of the first and second sides configured to operate as a deisohexanizer column and the other side of the first and second side configured to operate as a hexane column to produce hexane.

3 Claims, 9 Drawing Sheets (51) Int. Cl.
*C07C 7/00* (2006.01)
*B01D 3/14* (2006.01)
*B01J 19/00* (2006.01)

(52) U.S. Cl.
CPC ............ *B01J 19/0013* (2013.01); *C07C 7/04* (2013.01); *C07C 7/163* (2013.01); *B01J 2219/00054* (2013.01)

(56) References Cited

U.S. PATENT DOCUMENTS

| | | | | |
|---|---|---|---|---|
| 6,407,303 | B1* | 6/2002 | O'Brien | C07C 13/10 585/734 |
| 6,759,563 | B1* | 7/2004 | Hibbs | C07C 5/2791 585/737 |
| 7,223,898 | B2* | 5/2007 | Rice | C07C 5/2791 585/734 |
| 10,118,875 | B1* | 11/2018 | Kockler | C10G 7/02 |
| 10,500,522 | B2 | 12/2019 | Bhargava et al. | |
| 2006/0205990 | A1* | 9/2006 | Rice | C07C 5/2791 585/738 |
| 2012/0004478 | A1 | 1/2012 | Umansky et al. | |
| 2013/0068609 | A1 | 3/2013 | Bhargava et al. | |
| 2016/0311732 | A1 | 10/2016 | Banerjee et al. | |
| 2018/0282245 | A1* | 10/2018 | Kockler | C07C 5/2732 |
| 2019/0083898 | A1 | 3/2019 | Bhargava et al. | |
| 2022/0002215 | A1* | 1/2022 | Hamilton | B01D 3/141 |
| 2022/0033327 | A1* | 2/2022 | Piszczek | B01D 3/143 |

FOREIGN PATENT DOCUMENTS

| | | |
|---|---|---|
| CN | 104130094 A | 11/2014 |
| CN | 106458792 A | 2/2017 |
| CN | 207047164 U | 2/2018 |

OTHER PUBLICATIONS

Viacheslav A. Chuzlov; et al.; "Simulation of Light Naphtha Isomerization Process"; ScienceDirect; 16th International Scientific Conference "Chemistry and Chemical Engineering in XXI century"; Procedia Chemistry; c. 2015; pp. 282-287.
https://en.wikipedia.org/wiki/Heterogeneous_catalysis.
International Search Report dated Aug. 28, 2020 in corresponding International Application No. PCT/IB2020/000379.
Chinese Office Action dated Aug. 30, 2022 in corresponding Chinese Application No. 202080036029.9.

* cited by examiner

HEXANE AS A BY-PRODUCT OF ISOMERIZATION UNIT USING A DIVIDING WALL COLUMN

CROSS-REFERENCE TO RELATED APPLICATIONS

This application is a U.S. National Stage application of International Application No. PCT/IB2020/000379, filed May 14, 2020, which claims priority to U.S. Provisional Patent Application No. 62/848,217 filed on May 15, 2019, the contents of each of which are hereby incorporated by reference.

BACKGROUND

Field of the Invention

High-purity hexane is a light distillate product with a very narrow boiling range. It is used as a solvent in vegetable oil extraction processes, polymer processes, and in the drug and pharmaceutical industries. A special boiling point ("SBP") product, usually consisting of hydrocarbons with between 5 and 10 carbon atoms and having a distillation range between 55 and 155° C., is also a light distillate used in the paint industry.

Background Information

Figure 1:
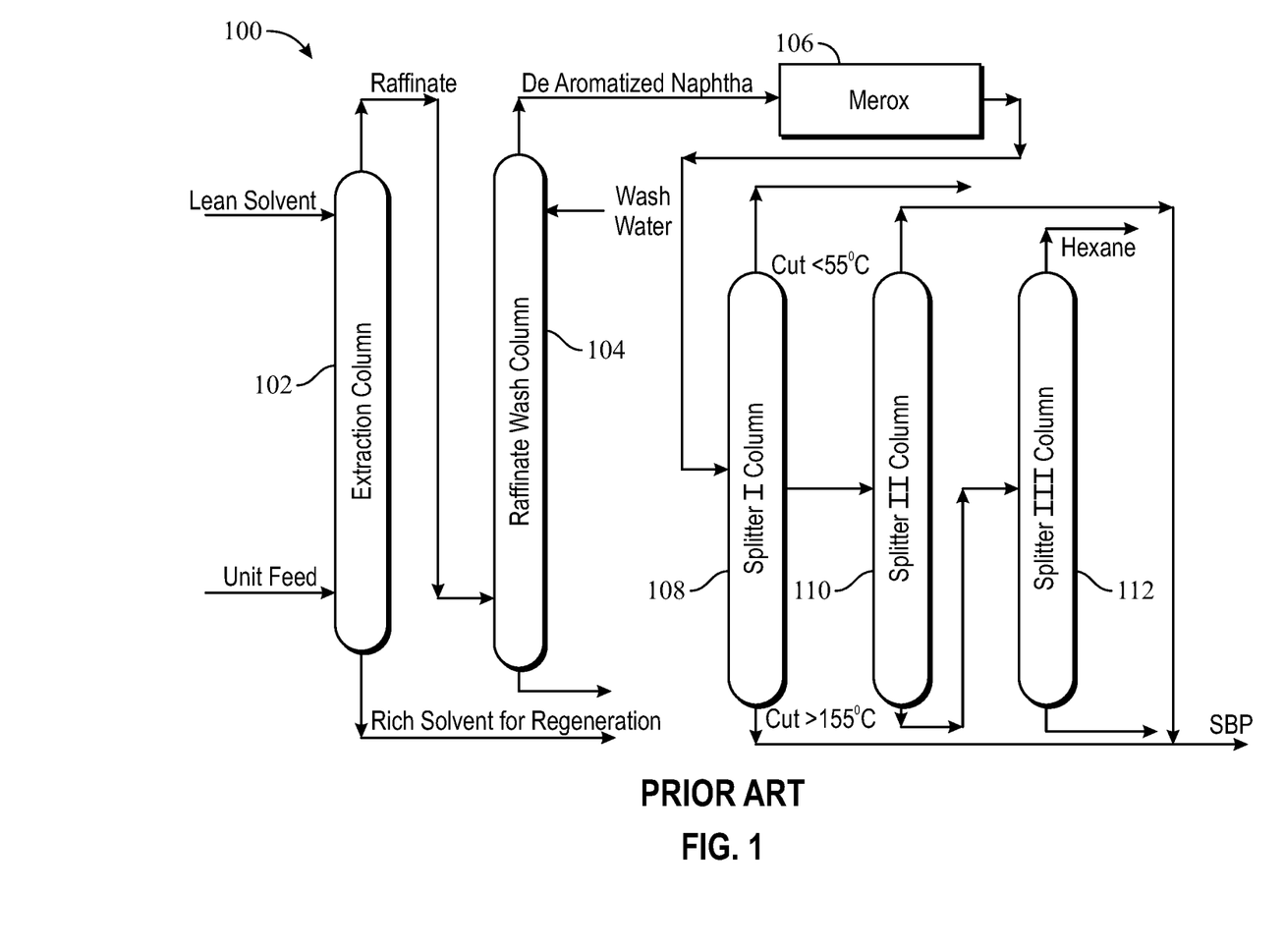
FIG. 1 represents a process flow scheme for production of hexane in accordance with the prior art.

Traditionally, hexane and SBP product are produced by a solvent extraction process. FIG. 1 illustrates a conventional solvent extraction process flow scheme 100 for producing hexane and SBP by carrying out extraction of naphtha cut (initial boiling point "IBP"—140° C.) using a solvent. Solvent and naphtha are fed to an extraction column 102. The solvent selectively extracts aromatics from the naphtha, producing a low aromatics content stream called raffinate. Raffinate from extraction column 102 is fed to a raffinate wash column 104 where the raffinate is water washed to remove traces of solvent from the raffinate. The dearomatized naphtha, so obtained, is then treated in a mercaptan removal unit 106 to meet a sulfur specification. The dearomatized naphtha is then fractionated in a series of three splitter columns 108, 110, 112 to produce the desired hexane and SBP cuts. While the process of FIG. 1 does produce hexane, the quality is inferior. For example, the benzene and sulfur content of hexane produced by the solvent extraction process of FIG. 1 is high (max. 500 ppm wt. and 5 ppm wt. respectively).

Figure 2:
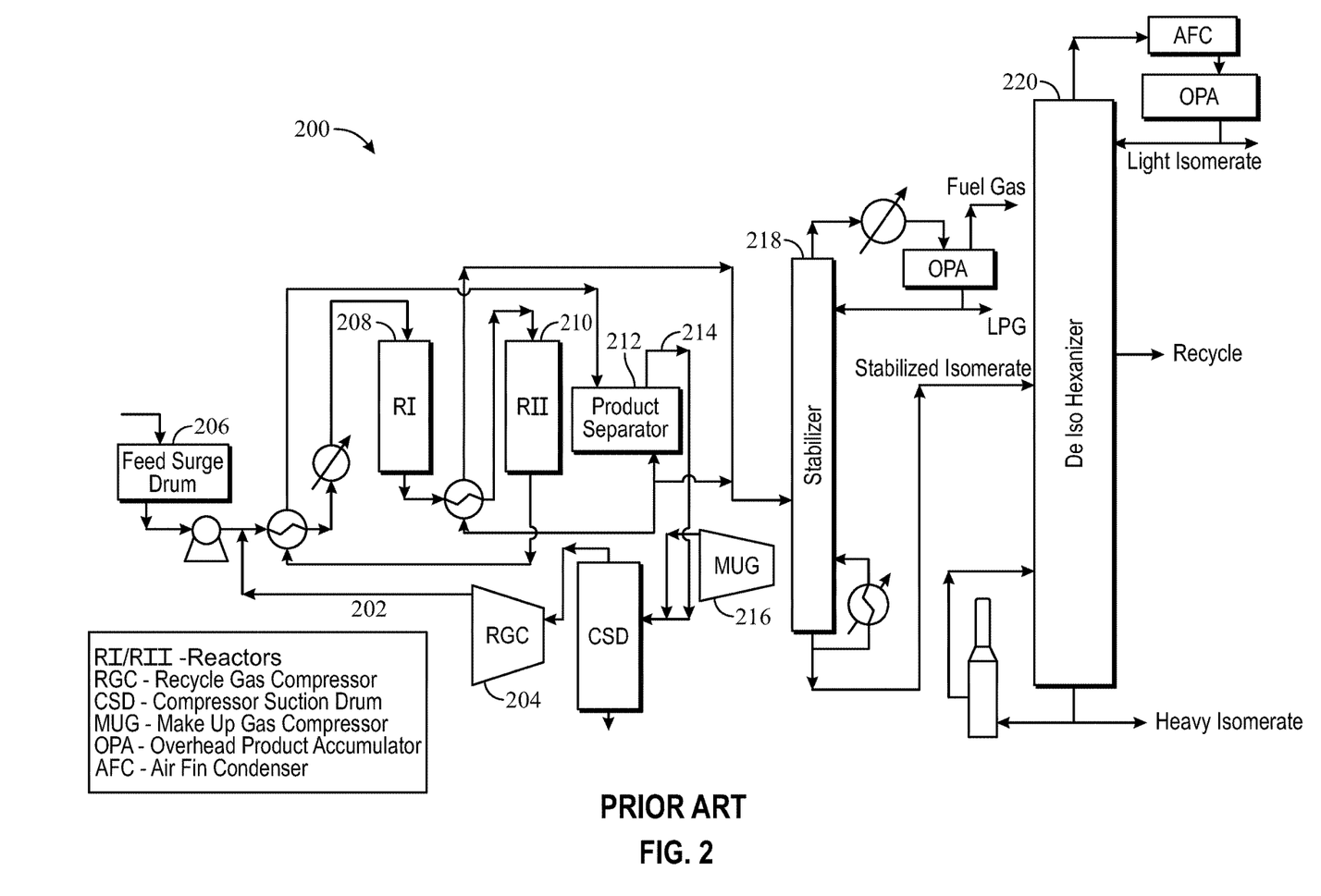
FIG. 2 represents the process flow scheme of an isomerization unit for the production of only isomerate as the desired product in accordance with the prior art.

Processing via isomerization saturates benzene and upgrades the octane of the light naphtha fraction (<80° C. boiling point). FIG. 2 illustrates a conventional isomerization process flow scheme 200. As shown in FIG. 2, feed and recycle gas 202 from a recycle gas compressor (RGC) 204, is preheated in a reactor feed-effluent exchanger 206 to a desired temperature before being routed to a series of reactors, for example reactor one ("RI") 208 and reactor two ("RII" 210), in which saturation of aromatics and conversion of normal paraffins to iso-paraffins takes place. Gas and liquid in the reactor effluent are separated in a product separator 212. Gas 214 from the product separator 212 is recycled back, using the RGC 204, to a reaction section after adding makeup hydrogen by using a makeup gas (MUG) compressor 216. Liquid, from the product separator 212, is routed to a stabilizer 218 for stabilization by removal of gas and liquefied petroleum gas (LPG) from the liquid. The stabilized isomerate is then split in a De-Iso-Hexanizer (DIH) column 220 to produce isomerate, meeting the specification of octane etc. Isomerate, thus produced, is a blend component of the refinery gasoline pool. The isomerization process flow scheme 200 produces only isomerate as the desired product.

SUMMARY

The present invention relates to a dividing wall column system for producing hexane, the dividing wall column system comprising:

a dividing wall column comprising a dividing wall that divides the dividing wall column at least partially into a first side and a second side, with one of the first and second sides preferably configured to operate as a deisohexanizer column and the other side of the first and second side preferably configured to operate as a hexane column to produce hexane.

Preferably, during operation of the dividing wall column system, the production of high-purity hexane involves taking a narrow cut of a hexane rich stream (32-45 wt % n-$C_6$). Since the feed consists of many components (e.g., $C_5$, $C_6$ paraffins, $C_6$ isoparaffins and $C_6$ naphthenes) with similar relative volatility, the process to produce high-purity hexane is quite energy intensive. The use of dividing wall column ("DWC") technology significantly improves the viability of this process by enabling the separation to take place in the same column shell by avoiding back mixing of the heaviest components with the middle boiling components. Due to the segregation of the column, an adequate number of trays are available on each side to facilitate an efficient separation of the components. As compared to a two column process scheme, the DWC scheme requires less energy and less equipment for the same separation. Hence, a DWC improves profitability for high-purity hexane production. In particular, the operating costs are about 20 to 70% lower than those of a solvent extraction process, such as one shown in FIG. 1.

In accordance with a particular preferred embodiment of the present invention, the dividing wall column system further comprises a hexane polishing unit connected with the dividing wall column so that the hexane produced in the dividing wall column is transferred into the hexane polishing unit, wherein the hexane polishing unit comprises a hexane polishing reactor for hydrogenating at least a part of the benzene included in the produced hexane. A hexane polishing unit means in accordance with the present invention any unit being configured to hydrogenate at least a part of the benzene included in the hexane being produced in the dividing wall column so as to reduce the benzene content of the hexane to a desired value. Thus, the hexane polishing unit can also be designated as benzene saturation unit or benzene hydrogenation unit. The hydrogenation itself takes place in the hexane polishing reactor, whereas the hexane polishing unit preferably comprises in addition to the hexane polishing reactor devices for feeding hydrogen into the unit, for mixing the hydrogen with the hexane being produced in the dividing wall column, for preheating this mixture before being fed into the hexane polishing reactor and the like.

In view of this, it is preferred that the hexane polishing unit further comprises a mixer for mixing the hexane being produced in the dividing wall column and hydrogen, wherein the mixer is arranged upstream of the hexane polishing reactor.

In a further development of embodiments of the present invention, it is proposed that the hexane polishing unit further comprises a stripper column for separating lights from the hexane, wherein the stripper column is preferably arranged downstream of the hexane polishing reactor.

In order to adjust an optimal temperature for the hexane/hydrogen-mixture introduced into the hexane polishing reactor, it is proposed that the hexane polishing unit further comprises one or more heat exchangers.

In accordance with a further preferred embodiment of the present invention, the dividing wall of the dividing wall column does not extend over the whole height of the dividing wall column, so that the dividing wall column comprises a portion with the first side and the second side being divided by the dividing wall arranged therebetween, and one or two further portions being not divided by the dividing wall. Each of the first side and the second side preferably comprises, independently from each other, 10 to 70 theoretical stages, wherein the one or two further portions preferably comprise in sum 10 to 50 theoretical stages. Preferably, the dividing wall is arranged vertically in the dividing wall column.

More preferably, each of the first side and the second side comprises, independently from each other, 30 to 60 theoretical stages and the one or two further portions comprise in sum 30 to 40 theoretical stages.

In accordance with one embodiment of the present invention, the number of theoretical stages of the first side and the number of theoretical stages of the second side are the same.

In accordance with an alternative embodiment of the present invention, the number of theoretical stages of the first side and the number of theoretical stages of the second side are the different. It is preferred in this embodiment that one of the first and second side has 20 to 30 theoretical stages more than the other of the two sides. For instance, good results are obtained, when the first side has 10 to 80 theoretical stages and the right side has 10 to 40 theoretical stages or vice versa.

Figure 7:
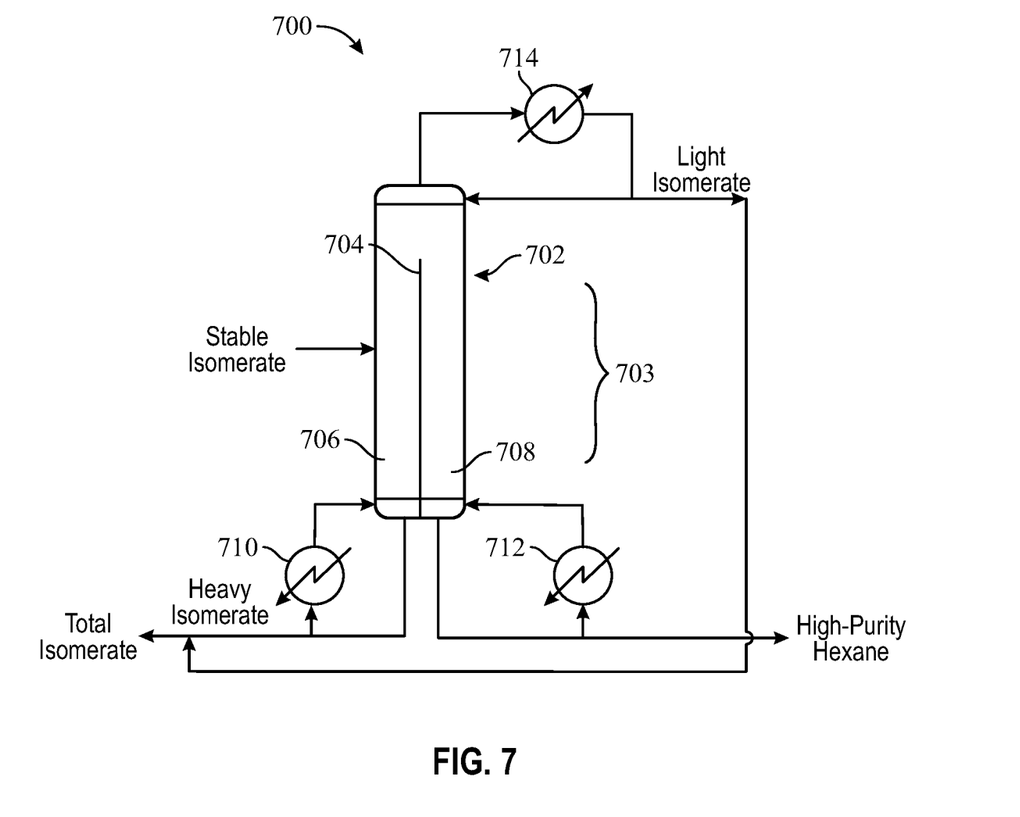
FIG. 7 illustrates a process scheme using a DWC with a bottom dividing wall in accordance with embodiments of the disclosure.
Figure 8:
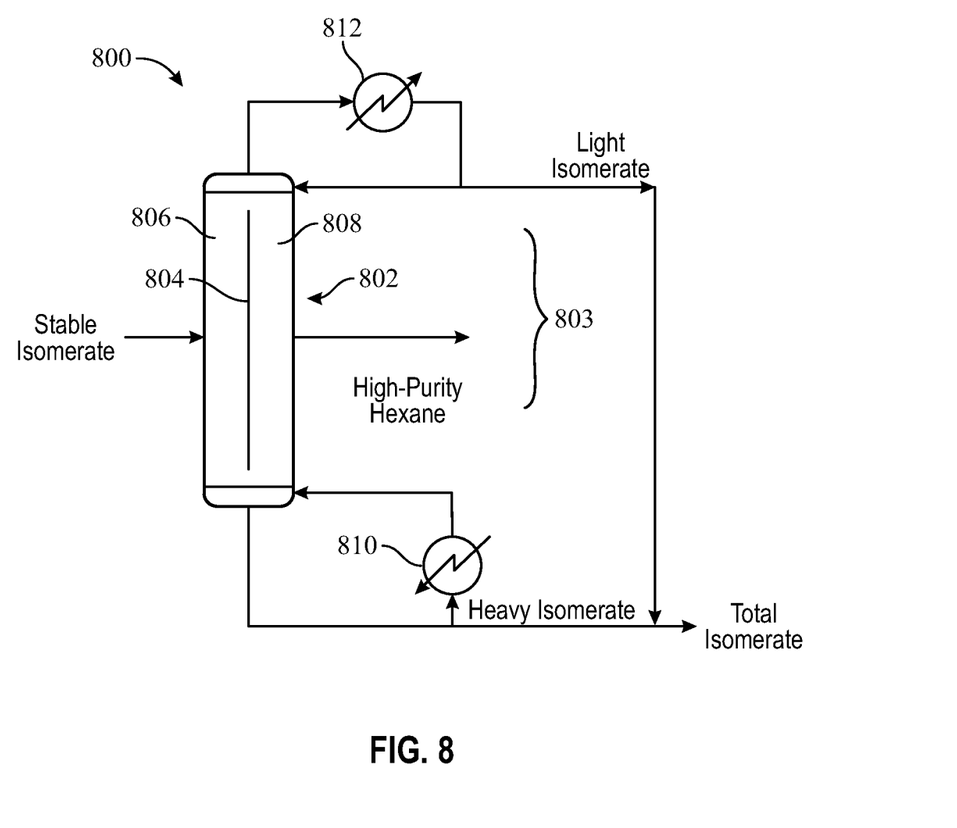
FIG. 8 illustrates a process scheme using a DWC with a middle dividing wall in accordance with embodiments of the disclosure.

The dividing wall can be located anywhere in the column, such as, for example, in a top section (FIG. 6), a bottom section (FIG. 7), or a middle section (FIG. 8). During operation, the process uses the DWC to produce a light isomerate fraction and a heavy isomerate fraction as the top and bottom products, respectively. A high-purity n-$C_6$ product can be withdrawn as the middle cut. As set out above, the process produces similar product specifications with much lower energy costs as compared to a two-column distillation process scheme for the same feed.

In accordance with a first particular preferred embodiment of the present invention, the dividing wall column is a DWC with a top dividing wall configuration, i.e. the dividing wall is a (preferably vertically arranged) top dividing wall positioned in the top portion of the dividing wall column, with the first side being a first fractionation section and the second side being a second fractionation section. Due to the presence of a dividing wall in the top of the column, the top portion of the column has two independent rectifying sections (i.e., on either side of the dividing wall) with a common stripping section. Each rectifying section is preferably equipped with an independent overhead system. Similarly, the stripping section (i.e., the bottom section below the dividing wall) is preferably equipped with a thermosiphon reboiler. The invention is similar in operation to a two-column separation sequence comprising a DIH column and a hexane column in which high-purity hexane is the middle cut. In the rectifying zone on the feed side, due to pre-fractionation the lightest boiling components are collected as lights at the top. The middle boiling components (mainly a mix of $C_{6s}$) and the heaviest components (mainly i-$C_6$ and heavier) move towards the bottom of the column. The heating duty provided by the reboiler helps to move the middle boiling components up the other side of the top dividing wall. The middle boiling components are eventually concentrated at the top on this side of the DWC., Preferably, the DWC that includes a top wall, the DWC has two independent overhead systems, one on either side.

Moreover, it is preferred that the dividing wall is placed in this embodiment between the first and second side, seen from top to bottom of the dividing wall column, between the theoretical stage 1 (i.e. the uppermost part of the dividing wall column, which is the first stage of the dividing wall column) and the theoretical stage 100 of the dividing wall column in the first side, i.e. the dividing wall extends from the top of the dividing wall column to the last theoretical stage of the first side, which is preferably theoretical stage 100 seen from the first side of the dividing wall column. If the second side of the dividing wall column comprises the same number of theoretical stages as the first side, this corresponds to the theoretical stage 100 seen from the second side of the dividing wall column. However, if the second side of the dividing wall column comprises a different number of theoretical stages as the first side, this corresponds to whatever is the last theoretical stage of the second side.

Preferably, the feed is placed in the top column embodiment on the first side between the theoretical stage 20 and the theoretical stage 60 of the first side. Since the dividing wall extends from the uppermost part of the dividing wall column until the last theoretical stage of the first side, this corresponds to between the theoretical stage 20 and the theoretical stage 60 of the dividing wall column.

Moreover, it is preferred in this embodiment that the dividing wall column system further comprises a first overhead condenser in fluid communication with the first fractionation section and a second overhead condenser in fluid communication with the second fractionation section.

It is also preferred that the dividing wall column system further comprises a reboiler in fluid communication with the bottoms section of the dividing wall column.

In accordance with a second particular preferred embodiment of the present invention, the dividing wall column is a DWC with a bottom dividing wall, i.e. the dividing wall is a (preferably vertically arranged) bottom dividing wall positioned in the bottom portion of the dividing wall column, with the first side being a first fractionation section and the second side being a second fractionation section. Unlike a DWC with a top dividing wall, a DWC with a bottom dividing wall has two independent stripping sections (i.e., on either side of the dividing wall) with a common rectifying section (i.e., the top section above the dividing wall). The feed is introduced on a pre-fractionation side of the DWC, wherein the heaviest boiling components are separated at a bottom of the DWC. The lightest boiling components are recovered at a top of the DWC. The middle boiling components are concentrated at the bottom on the other stripping section and removed as a separate product. Preferably, in the DWC with a bottom dividing wall, each stripping section is equipped with a thermosiphon reboiler. The DWC has a common rectifying zone with a single overhead system.

Preferably, the dividing wall is placed in this embodiment between the first and second side, seen from top to bottom of the dividing wall column, between the theoretical stage 20 and the last theoretical stage (i.e. the lowermost part) of the dividing wall column.

It is further preferred that the dividing wall column system further comprises a first reboiler in fluid communication with the first fractionation section, and a second reboiler in fluid communication with the second fractionation section. Good results are in particular obtained, when the first reboiler is a thermosiphon reboiler and/or the second reboiler is a thermosiphon reboiler.

In addition, it is preferred that the dividing wall column system further comprises a common rectifying section in fluid communication with the top portion of the dividing wall column.

In accordance with a third particular preferred embodiment of the present invention, the dividing wall column is a DWC with a middle dividing wall configuration, i.e. the dividing wall is a (preferably vertically arranged) middle dividing wall positioned in the middle portion of the dividing wall column, with the first side being a first fractionation section and the second side being a second fractionation section. Due to the presence of a dividing wall in the middle of the column, the middle of the column has two independent sections (i.e., on either side of the dividing wall) with common top and bottom sections (i.e., the sections above and below the middle dividing wall). The top and bottom sections are equipped with an overhead system and a reboiler, respectively.

Preferably, the dividing wall is placed in this embodiment between the first and second side, seen from top to bottom of the dividing wall column, between the theoretical stage 20 of the dividing wall column and the last theoretical stage of the first side of the dividing wall column.

Moreover, it is preferred that the feed is placed in this embodiment on the first side between the theoretical stage 30 of the dividing wall column and the theoretical stage 60 of the dividing wall column. The hexane stream outlet is preferably placed on the second side between the theoretical stage 40 of the dividing wall column and the theoretical stage 60 of the dividing wall column.

Good results are in particular obtained, when the dividing wall column system further comprises a thermosiphon reboiler configured to receive a bottoms product from the dividing wall column and an overhead system configured to receive a lights product from the dividing wall column.

In accordance with a further aspect, the present invention relates to a method of producing hexane, wherein the method comprises producing, as a byproduct from a $C_{5/6}$-isomerization unit, hexane using a dividing wall column system as described above. Byproduct means in this connection less than 20 vol.-% of the sum of all product streams.

In particular, it is preferred that embodiments of the method comprise the steps of feeding a stable isomerate feed to the first side of the dividing wall column; of producing a hexane feed from the second side of the dividing wall column; feeding the hexane feed to the hexane polishing unit. More specifically, the hexane feed and hydrogen are preferably fed to a mixer of the hexane polishing unit to form a hexane-hydrogen mixture.

Preferably, the feed is the isomerate stream produced in an isomerization unit and preferably a $C_5$-$C_6$-isomerization unit. The feed can e.g. comprise mainly $C_4$-$C_7$-hydrocarbons, such as $C_4$-$C_7$-n-paraffins, isoparaffins, naphthenes and aromatics. However, it can also be a narrow $C_5$-$C_6$-cut, such as one comprising $C_5$-$C_6$-n-paraffins, isoparaffins, naphthenes and aromatics.

In accordance with a further preferred embodiment of the present invention, the method further comprises the steps of preheating the hexane-hydrogen mixture; and of feeding the preheated hexane-hydrogen mixture to a polishing reactor of the hexane polishing unit.

Good results are in particular obtained, when the method further comprises the step of feeding an output stream from the polishing reactor to a stripper column of the hexane polishing unit for separating lights from the hexane, wherein the stripper column is preferably arranged downstream of the hexane polishing reactor.

In order to further increase the efficiency of the method, it is proposed in a further development of the present invention that in the method the preheating comprises the steps of exchanging heat between the hexane-hydrogen mixture and the feed from the stripper column in a first heat exchanger; and exchanging heat between the hexane-hydrogen mixture and the output stream from the polishing reactor in a second heat exchanger.

An exemplary system and process, according to embodiments of the disclosure, is directed to the production of SBP (55-115° C.) as a blend of the side cut of the DWC with light isomerate and a heavier naphtha cut from the isomerization feed splitter.

An exemplary system and process, according to embodiments of the disclosure, is directed to the variable operating cost for the production of hexane, as a byproduct, from an isomerization unit. The operating cost, per ton of hexane produced, from isomerization unit is 20 to 70% or even 90% lower than the cost of hexane produced by a solvent extraction process, thereby appreciably reducing CO2 emissions. Moreover, preferably the hexane has an improved quality (such as improved with respect to sulfur, benzene and n-hexane content) compared to a quality of hexane produced by a solvent extraction process and/or the hexane meets specifications for use in food, pharmaceutical, and polymer processes.

In all embodiments of the disclosure, a column overhead pressure on either side of the dividing wall of the DWC is maintained via a pressure controller on the respective overhead vapor product lines. The overhead vapor (on each side in a top DWC) is condensed using air-cooled exchangers and collected in an overhead receiver.

An exemplary system and process, according to embodiments of the disclosure, includes a DWC with a top dividing wall. The two top halves on either side of the top dividing wall of the DWC receive reflux from respective overhead condensers. Preferably, the temperature in the top of the DWC is cascaded to a reflux flow control loop to allow control over a quality of the product. This control philosophy prevents the heavier components from going to the top of the DWC. Similarly, the heaviest bottom product flow rate (on each side in a bottom DWC) is controlled by cascading with a level control loop in the lower section.

An exemplary system and process, according to embodiments of the disclosure, is directed toward production of high purity hexane as a byproduct from an isomerization unit. Stabilized isomerate is split in the DWC to co-produce hexane from the second side of the column. The hexane, so produced, is treated in a polishing unit comprising of an adsorbent section and a stripper section. Hexane produced from the isomerization unit has a benzene content of <3 ppm wt., a sulfur content of <0.5 ppm wt. (passing the test for poly cyclic aromatics (PCA)), and an n-hexane content of >40%. The quality of hexane produced, as a byproduct from isomerization unit, is much superior to that produced by the traditional solvent extraction process.

BRIEF DESCRIPTION OF THE DRAWINGS

The invention will be explained in more detail hereinafter with reference to the drawings.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

In the instant disclosure, an isomerization unit deisohexanizer ("DIH") column is a dividing wall column (DWC) and is used to produce hexane, as a byproduct, along with the main product of isomerate. An n-hexane rich product (about 32-45 wt % n-$C_6$) is obtained from the isomerization unit DIH column. Other $C_6$ components (e.g., 2-methylpentane, 3-methylpentane and methylcyclopentane) make up the rest of the product. Besides high-purity n-hexane, the other products from the isomerization unit column are light isomerate (mainly i-$C_5$) and heavy isomerate (mainly i-$C_6$).

Figure 3:
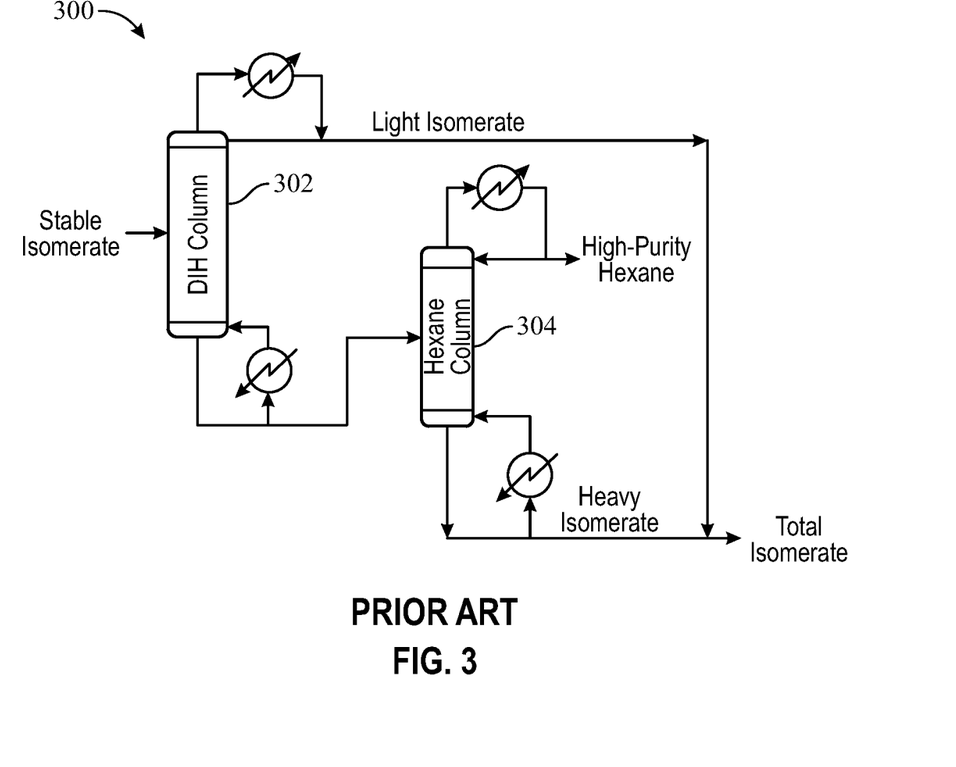
FIG. 3 represents the conventional process scheme of a high-purity hexane column in conjunction with a deisohexanizer in accordance with the prior art.

Conventionally, high-purity hexane can be obtained by distillation in a deisohexanizer column followed by a hexane column. FIG. 3 illustrates a prior art system 300 for producing high-purity hexane. System 300 includes a DIH column 302 and a hexane column 304. Bottoms from DIH column 302 are fed to hexane column 304. Hexane column 304 produces high-purity hexane and heavy isomerate. System 300 has certain disadvantages. For example, the boiling points of $C_6$ components are very close to that of the non-desirable components (e.g., $C_5$ paraffins and naphthenes). To obtain good separation, the process of system 300 requires a significant number of trays (leading to a bigger column) as well as high reboiling energy.

Figure 4:
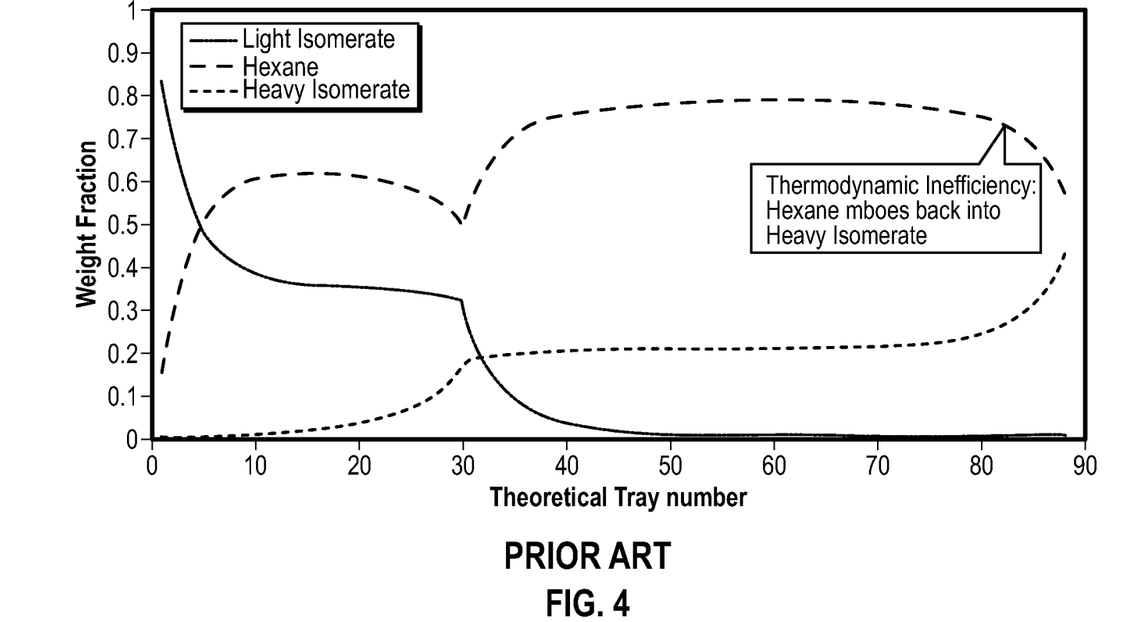
FIG. 4 represents the concentration profile inside a conventional deisohexanizer column in accordance with the prior art.
Figure 5:
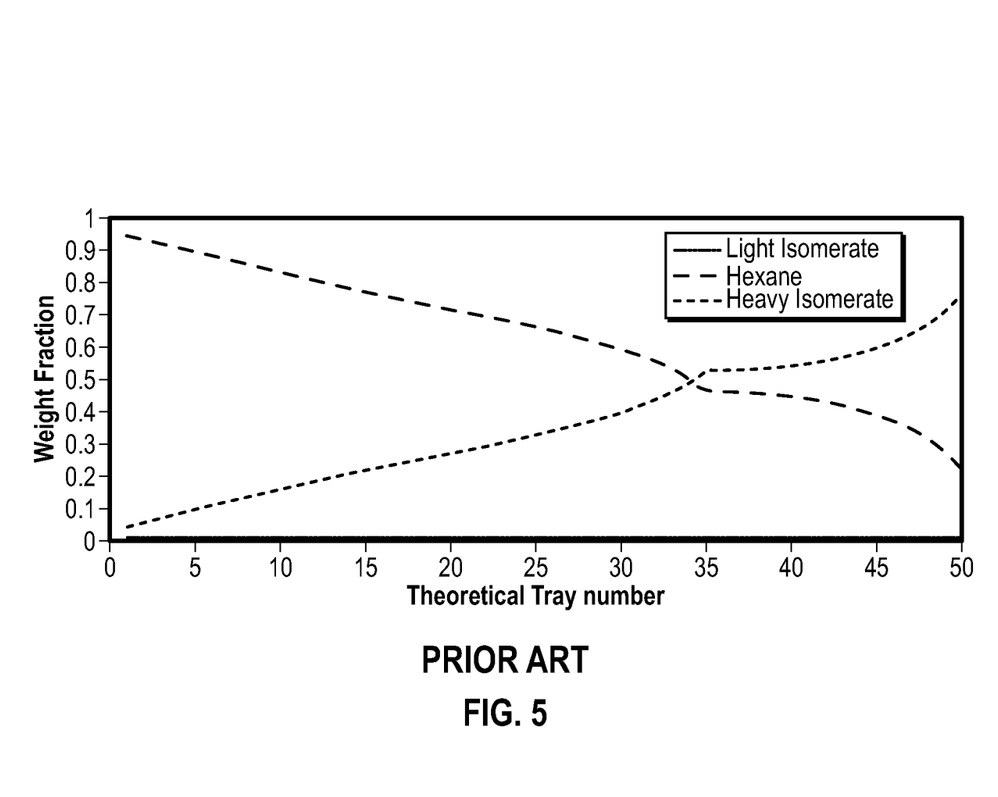
FIG. 5 is a graph illustrating a concentration profile inside a conventional hexane column in accordance with the prior art.

Systems with two columns also have the problem of back-mixing of a concentrated hexane stream within the DIH column. Thus, the energy spent in concentrating the hexane stream to higher purity levels is lost due to the back-mixing of hexane with the heavy isomerate at the bottom of the column. The concentration profiles of light isomerate, hexane, and heavy isomerate fractions in the DIH column are shown in FIG. 4. Additional energy is spent in the hexane column (see FIG. 5) to separate the hexane from the heavy isomerate, thereby reducing an overall energy efficiency of the process.

A solution to this thermodynamic problem is to separate the hexane from the heavy isomerate at the peak of its concentration within DIH column 302 to optimize an energy requirement of system 300. Furthermore, since two columns are required for the process, capital costs increase due to additional equipment and bigger plot space. For such applications, a DWC concept can be applied to provide an alternative solution.

Figure 6:
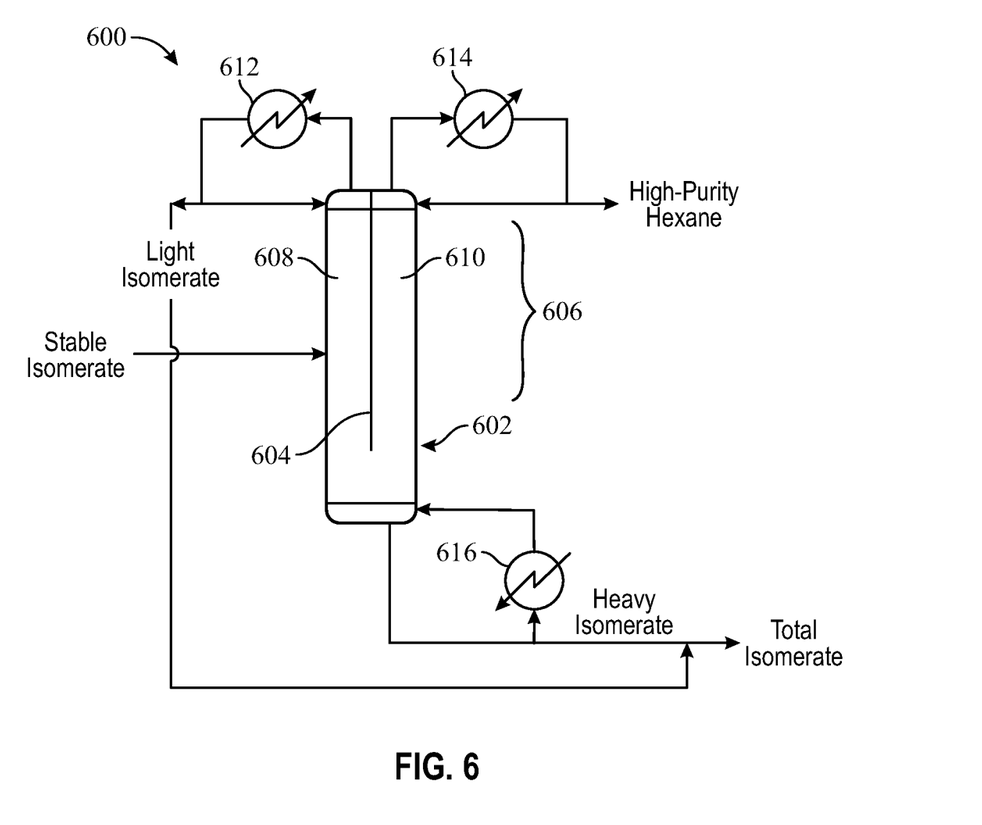
FIG. 6 illustrates a process scheme using a DWC with top dividing wall in accordance with embodiments of the disclosure.

A DWC combines operations of the two columns (e.g., DIH column 302 and hexane column 304) into a single column thereby lowering both the capital and energy (operating) costs by approximately 20-30%. In general, dividing wall columns are broadly classified into three types based on the location of a wall disposed with the DWC. The wall can be located in top section, a middle section, or a bottom section. In a DWC scheme, three (or four) products are typically withdrawn from the DWC: a lightest cut and a heaviest cut are withdrawn at the top and bottom, respectively, of the DWC; and a middle cut is obtained from the DWC as a side cut. In a majority of DWCs in operation worldwide, the dividing wall is present in a middle section of the DWC. In DWCs, a location of the dividing wall primarily dictates the movement of vapor within the column and can affect a quality of the separation. The dividing wall in a DWC leads to the splitting of the top (or bottom or middle) half of the column into two separate columns, which produces two high-purity products at the top (or bottom or middle). Top, bottom, and middle dividing walls are shown in FIGS. 6, 7, and 8, respectively. A feed (e.g., stable isomerate) is introduced on one side of the dividing wall (pre-fractionation) and the side cut is withdrawn from the other side (main fractionation). The process scheme is similar to that of a direct or indirect sequence of a two-column conventional separation.

The systems of FIGS. 6-8 have several advantages. For example, FIG. 6 illustrates a top DWC system 600 that includes a top DWC 602. A top dividing wall 604 divides a top section 606 of top DWC 602 into a first side 608 and a second side 610. Top dividing wall 604 extends from a top of top DWC 602 and terminates above a bottoms section of DWC 602. By incorporating top dividing wall 604 at the top of top DWC 602, first side 608 and second side 610 remain isolated from one another with no chance of contamination or back-mixing. Because first side 608 and second side 610 are two parallel sections created in a single column, a higher number of trays are available to achieve better fractionation within the same column. This tends to reduce the final height of the column by lowering the number of trays required. Lastly, first side 608 and second side 610 operate independent of each other. One side can operate as a rectification section while the other side can operate as the absorption (or rectification) section, with independent controls on each side. In this type of DWC, there are two separate overhead systems, a first overhead system 612 and a second overhead system 614. Each overhead system 612, 614 can include, for example, a heat exchanger (e.g., an air-cooled heat exchanger) and an overhead receiver.

First side 608 of top DWC 602 receives a stable isomerate feed (e.g., from an upstream process, such as an isomerization unit). Top DWC 602 outputs light isomerate as a lights product from first side 608 and high-purity hexane (e.g., having a hexane purity of 40 to 45 wt.-%) as a lights product from second side 610. A portion of the light isomerate can be returned to first side 608 as reflux and the remainder can be collected as a portion of total isomerate produced by top DWC system 600. Top DWC 602 also outputs heavy isomerate as a bottoms product. A portion of the bottoms product can be returned to top DWC 602 after passing through a reboiler 616 and the remainder can be output with the remainder of light isomerate as the other portion of the total isomerate output by top DWC 602. The heating duty provided by the reboiler helps to move the middle boiling components up the other side of the top dividing wall.

FIG. 7 illustrates a bottom DWC system 700 that includes a bottom DWC 702. Bottom DWC 702 works on a similar principle as that of top DWC 602 and includes a bottom dividing wall 704. Bottom dividing wall 704 extends from a bottom of bottom DWC 702 and divides a bottom section 703 of the bottom DWC 702 into a first side 706 and a second side 708. Compared to top DWC system 600, bottom DWC 702 includes two bottom reboilers, a first reboiler 710 and a second reboiler 712, and a common rectifying section 714. Both sides 706, 708 in bottom DWC 702, are controlled independent of each other.

First side 706 of bottom DWC 702 receives a stable isomerate feed (e.g., from an upstream process, such as an isomerization unit). Bottom DWC 702 outputs light isomerate as a lights product from the top of bottom DWC 702 and high-purity hexane (e.g., having a hexane purity of 40 to 45 wt.-%) as a bottoms product from second side 708. A portion of the light isomerate can be returned to the top of bottom DWC 702 as reflux from common rectifying section 714 and the remainder can be collected as a portion of total isomerate produced by bottom DWC system 700. Bottom DWC 702 also outputs heavy isomerate as a bottoms product from first side 706. A portion of the heavy isomerate can be returned to first side 706 after passing through first reboiler 710 and the remainder can be output with the remainder of light isomerate as the other portion of the total isomerate output by bottom DWC 702.

FIG. 8 illustrates a middle DWC system 800 that includes a middle DWC 802. Middle DWC 802 works on a similar principal as that of top DWC 602 and bottom DWC 702 and includes a middle dividing wall 804. Middle dividing wall 804 extends the length of a middle portion 803 of middle DWC 802 and divides middle DWC 802 into a first side 806 and a second side 808 to pre-fractionate the feed and concentrate the middle boiling components on the second side 808 to produce a high-purity product. Middle dividing wall 804 does not extend all the way to the top or bottom of middle DWC 802. Middle DWC system 800 also includes a reboiler 810 and a rectifying section 812. As in the top and bottom DWCs 602, 702, there is no back-mixing of the feed and the side cut. This results in an efficient separation with lesser consumption of reboiling duty.

First side 806 of middle DWC 802 receives a stable isomerate feed (e.g., from an upstream process, such as an isomerization unit). Middle DWC 802 outputs light isomerate as a lights product from a top of middle DWC 802. A portion of the light isomerate can be returned to the top of middle DWC 802 as reflux and the remainder is output as a portion of the total isomerate produced by middle DWC 802. Middle DWC 802 outputs heavy isomerate as a bottoms product. A portion of the heavy isomerate can be returned to the bottom of middle DWC 802 after passing through reboiler 810 and the remainder is output as the other portion of the total isomerate produced by middle DWC 802. High-purity hexane (e.g., having a hexane purity of 40 to 45 wt.-%) is produced as a side cut from second side 808.

Figure 9:
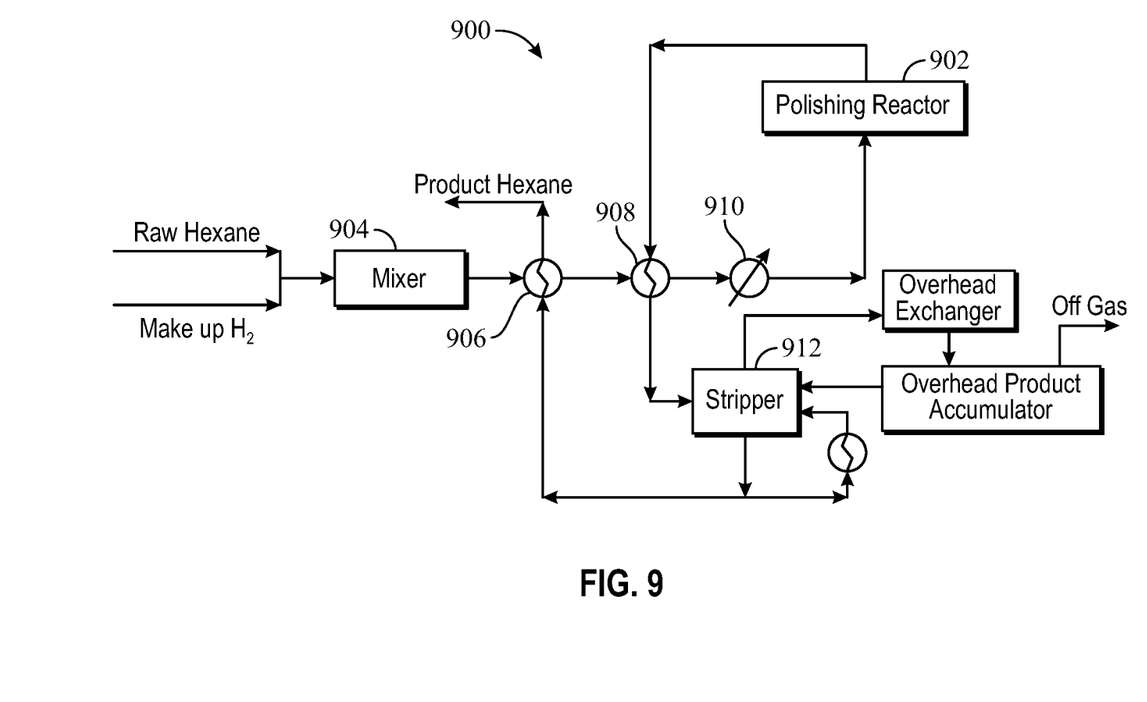
FIG. 9 illustrates a process scheme for a hexane polishing unit in accordance with embodiments of the disclosure.

FIG. 9 illustrates a system 900 for processing hexane in a polishing unit (polisher) comprising a polishing reactor 902, a mixer 904, three heat exchangers 906, 908, 910 and a hexane stripper column 912, to ensure that benzene content of the hexane is in a desired range. In some embodiments, the hexane is fed from an isomerization unit DWC. In the polishing unit, hydrogen and raw hexane are preheated before being routed through an adsorbent. The hydrogen and raw hexane are mixed in the mixer 904 prior to the preheating. The preheating can include heating from one or more heat exchangers. For example, as illustrated in FIG. 9, preheating can be accomplished via heat exchangers 906, 908, and 910. Heat exchanger 906 uses an output from the hexane stripper column 912 to heat the hydrogen/raw hexane feed. Heat exchanger 908 uses an output of the polishing reactor 902 to heat the hydrogen/raw hexane feed. Heat exchanger 910 uses an additional heat source (e.g., an upstream feed) to heat the hydrogen/raw hexane feed. In various embodiments, one or more of heat exchangers 906, 908, and 910 are optional. After adsorption, lights from polishing reactor 902 are separated from hexane in a hexane stripper column 912. The hexane from hexane stripper column 912 can be used as a heat source in heat exchanger 906, collected as an end product, or used as part of a downstream process.

The advantage of producing hexane, as a byproduct from isomerization unit, is that its quality is much superior to that produced by the traditional solvent extraction process. Hexane produced from isomerization unit meets specifications for food, pharmaceutical, and polymer grade hexanes. Additionally, the cost of production of hexane, as a byproduct from isomerization unit, is much lower than the cost of hexane produced by the solvent extraction process.

Examples

Tables 1-6 below demonstrate various operating parameters for conventional processes and systems and processes and systems of the instant disclosure that utilize DWCs.

TABLE 1

Performance of Conventional Design versus Dividing Wall Column Design

| | | Conventional | | DWC Design | | |
| | | | | Top Dividing | Bottom Dividing | Middle Dividing |
| Items Columns | Units | DIH Column | Hexane Column | Wall Column | Wall Column | Wall Column |
| Feed | kg/hr | 67,955 | | 67,955 | 67,955 | 67,955 |
| Light Isomerate | kg/hr | 43,262 | | 42,474 | 43,303 | 43,237 |

TABLE 1-continued

Performance of Conventional Design versus Dividing Wall Column Design

| Items Columns | Units | Conventional DIH Column | Conventional Hexane Column | DWC Design Top Dividing Wall Column | DWC Design Bottom Dividing Wall Column | DWC Design Middle Dividing Wall Column |
|---|---|---|---|---|---|---|
| Heavy Isomerate | kg/hr | 11,993 | | 12,862 | 11,934 | 12,106 |
| High-purity Hexane | kg/hr | 12,700 | | 12,700 | 12,700 | 12,700 |
| n-Hexane content | wt % | 39.4 | | 35.2 | 38.2 | 37.9 |
| Reboiler Duty | MMkcal/hr | 13.5 | 9.1 | 16.4 | 16.7 | 16.4 |
| Condenser Duty | MMkcal/hr | 16.8 | 9.2 | 19.8 | 20.1 | 19.7 |
| Energy Savings | % | — | | 27.4 | 26.1 | 27.4 |

TABLE 2

Material Balance of Conventional DIH Colum + Hexane Column

| Stream Description | Units | Feed | Light Isomerate | High-purity Hexane | Heavy Isomerate |
|---|---|---|---|---|---|
| Flowrate | kg/hr | 67,955 | 43,262 | 12,700 | 11,993 |
| Composition profile | | | | | |
| H2 | wt. % | 0.00 | 0.00 | 0.00 | 0.00 |
| C3− | wt. % | 0.00 | 0.00 | 0.00 | 0.00 |
| C4 Paraffins | wt. % | 0.29 | 0.46 | 0.00 | 0.00 |
| i-Pentane | wt. % | 8.40 | 13.19 | 0.00 | 0.00 |
| n-Pentane | wt. % | 2.68 | 4.21 | 0.00 | 0.00 |
| C5 Naphthenes | wt. % | 0.60 | 0.94 | 0.00 | 0.00 |
| C6 i-Paraffins | wt. % | 58.82 | 80.44 | 40.66 | 0.06 |
| Hexane | wt. % | 8.24 | 0.69 | 39.36 | 2.50 |
| C6 Naphthenes | wt. % | 16.08 | 0.07 | 19.97 | 69.69 |
| Benzene | wt. % | 0.00 | 0.00 | 0.00 | 0.00 |
| C7 Paraffins | wt. % | 2.22 | 0.00 | 0.00 | 12.57 |
| C7 Naphthenes | wt. % | 2.68 | 0.00 | 0.01 | 15.17 |
| Total | wt. % | 100.00 | 100.00 | 100.00 | 100.00 |
| Reboiler Duty | MMkcal/hr | | 13.5 + 9.1 | | |
| Condenser Duty | MMkcal/hr | | 16.8 + 9.2 | | |

TABLE 3

Material Balance of Top Dividing Wall Column

| Stream Description | Units | Feed | Light Isomerate | High-purity Hexane | Heavy Isomerate |
|---|---|---|---|---|---|
| Flowrate | kg/hr | 67,955 | 42,474 | 12,700 | 12,862 |
| Composition profile | | | | | |
| H2 | wt. % | 0.00 | 0.00 | 0.00 | 0.00 |
| C3− | wt. % | 0.00 | 0.00 | 0.00 | 0.00 |
| C4 Paraffins | wt. % | 0.29 | 0.46 | 0.00 | 0.00 |
| i-Pentane | wt. % | 8.40 | 13.44 | 0.00 | 0.00 |
| n-Pentane | wt. % | 2.68 | 4.29 | 0.00 | 0.00 |
| C5 Naphthenes | wt. % | 0.60 | 0.96 | 0.00 | 0.00 |
| C6 i-Paraffins | wt. % | 58.82 | 80.35 | 44.66 | 0.48 |
| Hexane | wt. % | 8.24 | 0.46 | 35.21 | 7.21 |
| C6 Naphthenes | wt. % | 16.08 | 0.04 | 20.13 | 66.41 |
| Benzene | wt. % | 0.00 | 0.00 | 0.00 | 0.00 |
| C7 Paraffins | wt. % | 2.22 | 0.00 | 0.00 | 11.74 |
| C7 Naphthenes | wt. % | 2.68 | 0.00 | 0.00 | 14.16 |
| Total | wt. % | 100.00 | 100.00 | 100.00 | 100.00 |
| Reboiler Duty | MMkcal/hr | | 16.4 | | |
| Condenser Duty | MMkcal/hr | | 17.0 + 2.8 | | |

TABLE 4

Material Balance of Bottom Dividing Wall Column

| Stream Description | Units | Feed | Light Isomerate | High-purity Hexane | Heavy Isomerate |
|---|---|---|---|---|---|
| Flowrate | kg/hr | 67,955 | 43,303 | 12,700 | 11,934 |
| Composition profile | | | | | |
| H2 | wt. % | 0.00 | 0.00 | 0.00 | 0.00 |
| C3− | wt. % | 0.00 | 0.00 | 0.00 | 0.00 |
| C4 Paraffins | wt. % | 0.29 | 0.46 | 0.00 | 0.00 |
| i-Pentane | wt. % | 8.40 | 13.28 | 0.00 | 0.00 |
| n-Pentane | wt. % | 2.68 | 4.25 | 0.00 | 0.00 |
| C5 Naphthenes | wt. % | 0.60 | 0.95 | 0.00 | 0.00 |
| C6 i-Paraffins | wt. % | 58.82 | 80.33 | 40.70 | 0.07 |
| Hexane | wt. % | 8.24 | 0.69 | 38.22 | 2.51 |
| C6 Naphthenes | wt. % | 16.08 | 0.04 | 21.08 | 69.53 |
| Benzene | wt. % | 0.00 | 0.00 | 0.00 | 0.00 |
| C7 Paraffins | wt. % | 2.22 | 0.00 | 0.00 | 12.64 |

TABLE 4-continued

Material Balance of Bottom Dividing Wall Column

| Stream Description | Units | Feed | Light Isomerate | High-purity Hexane | Heavy Isomerate |
|---|---|---|---|---|---|
| C7 Naphthenes | wt. % | 2.68 | 0.00 | 0.00 | 15.25 |
| Total | wt. % | 100.00 | 100.00 | 100.00 | 100.00 |
| Reboiler Duty | MMkcal/hr | | | 12.0 + 4.7 | |
| Condenser Duty | MMkcal/hr | | | 20.1 | |

TABLE 5

Material Balance of Middle Dividing Wall Column

| Stream Description | Units | Feed | Light Isomerate | High-purity Hexane | Heavy Isomerate |
|---|---|---|---|---|---|
| Flowrate | kg/hr | 67,955 | 43,237 | 12,700 | 12,106 |
| Composition profile | | | | | |
| H2 | wt. % | 0.00 | 0.00 | 0.00 | 0.00 |
| C3– | wt. % | 0.00 | 0.00 | 0.00 | 0.00 |
| C4 Paraffins | wt. % | 0.29 | 0.46 | 0.00 | 0.00 |
| i-Pentane | wt. % | 8.40 | 13.20 | 0.00 | 0.00 |
| n-Pentane | wt. % | 2.68 | 4.21 | 0.00 | 0.00 |
| C5 Naphthenes | wt. % | 0.60 | 0.94 | 0.00 | 0.00 |
| C6 i-Paraffins | wt. % | 58.82 | 80.40 | 40.87 | 0.07 |
| Hexane | wt. % | 8.24 | 0.69 | 37.94 | 4.22 |
| C6 Naphthenes | wt. % | 16.08 | 0.09 | 20.68 | 68.69 |
| Benzene | wt. % | 0.00 | 0.00 | 0.00 | 0.00 |
| C7 Paraffins | wt. % | 2.22 | 0.00 | 0.22 | 12.25 |
| C7 Naphthenes | wt. % | 2.68 | 0.00 | 0.28 | 14.76 |
| Total | wt. % | 100.00 | 100.00 | 100.00 | 100.00 |
| Reboiler Duty | MMkcal/hr | | | 16.4 | |
| Condenser Duty | MMkcal/hr | | | 19.7 | |

TABLE 6

Comparison of Quality of Hexane produced by the Solvent Extraction Process vs from Isomerization Unit

| | | Solvent Extraction Process | Isomerization Unit |
|---|---|---|---|
| n-hexane | % wt. | | >40 |
| Sulfur | mg/kg | 1.0-5.0 | <0.5 |
| Benzene | mg/kg | 130-240 | <3.0 |

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," "generally," "around," and "about" can be substituted with "within [a percentage] of" what is specified, where the percentage includes 0.1, 1, 5, and 10 percent.

The foregoing outlines features of several embodiments so that those skilled in the art can better understand the aspects of the disclosure. Those skilled in the art should appreciate that they can readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they can make various changes, substitutions and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A method of producing, as a by-product from a $C_5$-$C_6$-isomerization unit, hexane having a benzene content of <3 ppm wt., a sulfur content of <0.5 ppm wt. and an n-hexane content of >40 wt %, the method comprising:
   producing a stable isomerate feed in the $C_5$-$C_6$-isomerization unit,
   feeding the stable isomerate feed to a first side of a dividing wall column, the dividing wall column comprising a dividing wall that divides the dividing wall column at least partially into the first side and a second side, with one side of the first side and the second side configured to operate as a deisohexanizer column and the other side of the first side and the second side configured to operate as a hexane column to produce the hexane;
   producing a hexane feed from the second side of the dividing wall column;
   feeding the hexane feed and hydrogen to a mixer of a benzene hydrogenation unit connected with the dividing wall column to form a hexane-hydrogen mixture;
   preheating the hexane-hydrogen mixture;
   feeding the preheated hexane-hydrogen mixture to a polishing reactor of the benzene hydrogenation unit, wherein the polishing reactor hydrogenates at least a part of benzene included in the hexane-hydrogen mixture; and
   feeding an output stream from the polishing reactor to a stripper column for separating light components from hexane to form the hexane having the benzene content of <3 ppm wt., the sulfur content of <0.5 ppm wt. and the n-hexane content of >40 wt %, wherein the stripper column is arranged downstream of the polishing reactor.

2. The method of claim 1, wherein the preheating comprises
   exchanging heat between the hexane-hydrogen mixture and a feed from the stripper column in a first heat exchanger; and
   exchanging heat between the hexane-hydrogen mixture and the output stream from the polishing reactor in a second heat exchanger.

3. The method of claim 1, wherein one or more of the following are fulfilled:
   the hexane has an improved quality compared to a quality of hexane produced by a solvent extraction process,
   the hexane meets specifications for use in food, pharmaceutical, and polymer processes, and the method of producing hexane has a variable operating cost that is around 90% lower than hexane produced by a solvent extraction process.

* * * * *